(12) United States Patent
Pinto et al.

(10) Patent No.: US 8,608,657 B2
(45) Date of Patent: Dec. 17, 2013

(54) CLINICAL ACCEPTANCE TOOL

(75) Inventors: Yu Jung Pinto, Boulder, CO (US); Tracy Eliasson, Boulder, CO (US); Corinne Johnson, Denver, CO (US); Greg Lund, Boulder, CO (US); Bryan Hansen, Mead, CO (US)

(73) Assignee: Covidien LP, Mansfield, MA (US)

( * ) Notice: Subject to any disclaimer, the term of this patent is extended or adjusted under 35 U.S.C. 154(b) by 140 days.

(21) Appl. No.: 13/149,731

(22) Filed: May 31, 2011

(65) Prior Publication Data

US 2012/0310059 A1    Dec. 6, 2012

(51) Int. Cl.
*A61B 5/00* (2006.01)

(52) U.S. Cl.
USPC .......................... 600/301; 705/1.1

(58) Field of Classification Search
USPC ............................................ 705/2
See application file for complete search history.

(56) References Cited

U.S. PATENT DOCUMENTS

| | | | |
|---|---|---|---|
| 5,020,540 A | 6/1991 | Chamoun | |
| 6,839,581 B1 | 1/2005 | El-Sohl et al. | |
| 6,970,792 B1 | 11/2005 | Diab | |
| 7,252,636 B2 | 8/2007 | Brown | |
| 7,320,030 B2 | 1/2008 | Brown | |
| 7,440,787 B2 | 10/2008 | Diab | |
| 7,447,388 B2 | 11/2008 | Bates et al. | |
| 2003/0149371 A1 | 8/2003 | Shiga et al. | |
| 2005/0043894 A1* | 2/2005 | Fernandez | 702/19 |
| 2005/0066969 A1 | 3/2005 | Rick et al. | |
| 2006/0111749 A1 | 5/2006 | Westenskow et al. | |
| 2006/0241975 A1 | 10/2006 | Brown | |
| 2006/0285736 A1 | 12/2006 | Brown | |
| 2007/0016096 A1 | 1/2007 | Mcnabb | |
| 2007/0032732 A1 | 2/2007 | Shelley et al. | |
| 2007/0203406 A1 | 8/2007 | Anderson et al. | |
| 2007/0213619 A1 | 9/2007 | Linder | |
| 2007/0219059 A1 | 9/2007 | Schwartz et al. | |
| 2007/0225614 A1 | 9/2007 | Naghavi et al. | |
| 2008/0059249 A1 | 3/2008 | Joao | |
| 2008/0059250 A1 | 3/2008 | Joao | |
| 2008/0064965 A1 | 3/2008 | Jay et al. | |
| 2008/0081963 A1 | 4/2008 | Naghavi et al. | |

(Continued)

FOREIGN PATENT DOCUMENTS

| | | | |
|---|---|---|---|
| EP | 370637 A1 * | 5/1990 | ............... A61B 5/27 |
| WO | 99/62399 A1 | 12/1999 | |
| WO | 03096893 | 5/2002 | |
| WO | 2010/102069 A2 | 9/2010 | |

OTHER PUBLICATIONS

Mollot et al., Benchmarking a novel ultrasound—CT fusion system for respiratory motion, Med. Phys. 35 (1), Jan. 2008.*

(Continued)

*Primary Examiner* — John Pauls
*Assistant Examiner* — Jason Tiedeman

(57) ABSTRACT

Provided herein are methods and apparatuses for facilitating clinical acceptance of patient monitoring features. These methods may be used in conjunction with a computer that includes software for viewing the type of display associated with the monitoring feature. The clinical acceptance systems as provided herein may display a new or experimental monitoring feature along with a benchmark feature that a clinician is familiar with. In certain embodiments, the viewing tool may be isolated from the calculation tools so that the computer may include stored files that are in a format ready for display.

21 Claims, 5 Drawing Sheets

(56) References Cited

U.S. PATENT DOCUMENTS

| | | |
|---|---|---|
| 2008/0091088 A1 | 4/2008 | Kiani |
| 2008/0139889 A1 | 6/2008 | Bagan |
| 2008/0146892 A1* | 6/2008 | LeBoeuf et al. .............. 600/300 |
| 2008/0171311 A1 | 7/2008 | Centen et al. |
| 2008/0208011 A1 | 8/2008 | Shuler |
| 2008/0214903 A1 | 9/2008 | Orbach |
| 2009/0070342 A1* | 3/2009 | Uber et al. ....................... 707/10 |
| 2010/0057490 A1* | 3/2010 | Kocis et al. ....................... 705/2 |
| 2011/0040713 A1* | 2/2011 | Colman et al. ................. 706/16 |
| 2011/0105854 A1 | 5/2011 | Kiani et al. |

OTHER PUBLICATIONS

Kucewicz et al., Plethysmographic Arterial Waveform Strain Discrimination by Fisher'S Method, Ultrasound in Med. & Biol., vol. 30, No. 6, pp. 773-782, 2004.*

Gee et al., Processing and visualizing three-dimensional ultrasound data, The British Journal of Radiology, 77 (2004), S186-S193.*

Guerra et al., Real-Time Digital Timing in Positron Emission Tomography, IEEE Transactions on Nuclear Science, vol. 55, No. 5, Oct. 2008.*

International Search Report and Written Opinion for PCT No. PCT/US2012/040087 dated Sep. 21, 2012; 11 pages.

* cited by examiner

CLINICAL ACCEPTANCE TOOL

BACKGROUND

The present disclosure relates generally to medical monitors and, more particularly, to a user interface that presents medical monitor information for user review.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring device's have become an indispensable part of modern medicine.

Monitoring devices are often configured as dedicated monitoring units (e.g., a stand-alone pulse oximetry monitor) or a general purpose computer with integral processing circuitry for receiving measurements from medical devices and converting these measurements into medical information that is meaningful to a clinician. Accordingly, such devices typically include hardware and software capability for processing the data and supporting the graphical user interface that displays the data. The relationship between the received data and the displayed data may be complex. For example, raw data may be collected by a sensor and sent to the monitoring device to be amplified, filtered, digitized, calibrated, compared with empirical data, graphed, and/or otherwise processed. This processed data may then be converted to a metric or indicator for display that a clinician may correlate to a clinical condition. In a particular example, in a photoplethysmography system, an optical sensor may collect data from a photodetector and subject the data to a series of manipulations to convert the received photoplethysmography signal into one or more numerical indicators related to a patient's oxygen saturation or heart rate. The photoplethysmography data may also be graphed over time to provide information about ongoing trends. Accordingly, rather than displaying raw data, which may be difficult to interpret, the monitoring devices may present medical parameter data using graphical images or numerical indicators, which may be more user-friendly.

As clinicians have become more accustomed to having access to data from medical monitoring devices, their comfort with and ability to use the data provided by these devices has grown. Accordingly, these devices have achieved widespread clinical acceptance. However, at the same time, the capabilities of medical devices have also grown. For example, newer monitoring devices may be capable of presenting additional information related to the measured parameters or may be connected to different types of sensors that provide information about new parameters. As additional indicators and information are added to existing monitoring capabilities, clinical acceptance of these tools may be limited by a clinician's ability to understand and interpret the displayed data that is related to these indicators and/or information.

BRIEF DESCRIPTION OF THE DRAWINGS

Advantages of the disclosed techniques may become apparent upon reading the following detailed description and upon reference to the drawings in which.

DETAILED DESCRIPTION

Figure 1:
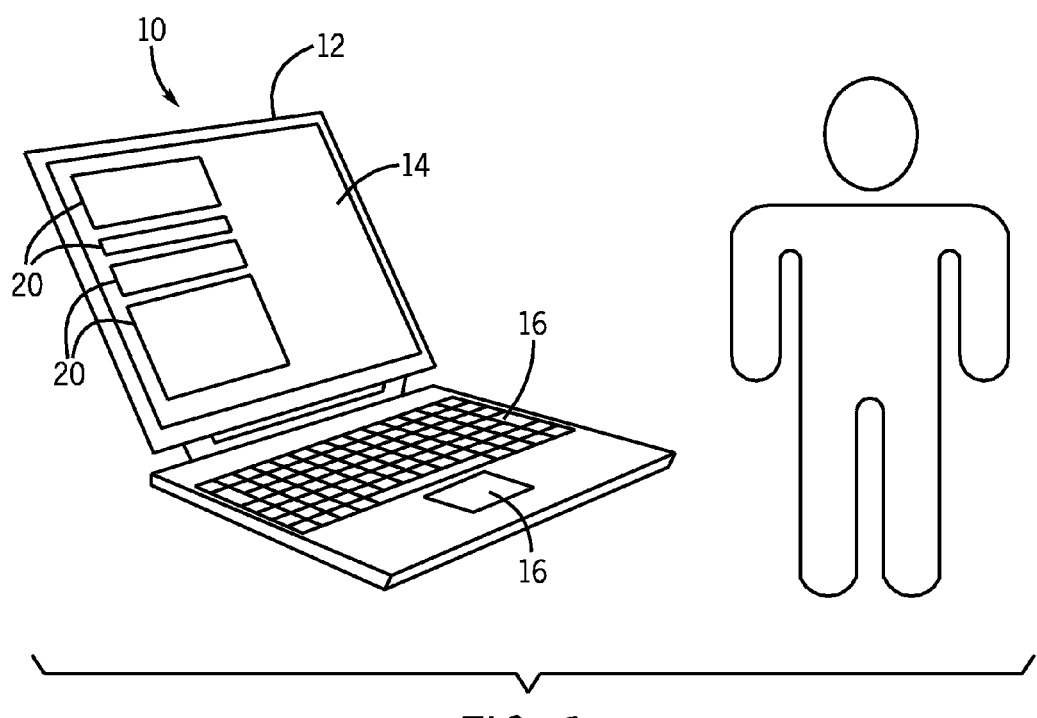
FIG. 1 is an example of a user interface for a clinical acceptance system in accordance with embodiments.

One or more embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are systems and methods for viewing clinical monitoring data for a physiological parameter. The systems as provided may facilitate clinical acceptance of new or different features available for a medical monitor. These systems may be used in conjunction with a viewing tool for end users of the medical monitor. As medical devices become increasingly sophisticated and incorporate additional monitoring features, it is desirable to have methods of training and presenting information for the healthcare professionals who will take advantage of the features of the device, such as information related to new capabilities of the device with which the user may be unfamiliar. In particular, the systems as provided herein facilitate understanding of the features of the medical monitor by presenting these features in graphical user interfaces that mimic or simulate the device when in use. Such systems may be incorporated into general purpose computers that may be used as training tools. In certain embodiments, these computers may be isolated from, i.e., may lack, the algorithms or processing circuitry of the medical device itself. In this manner, the training tool may be operated with lower processing power, because the clinical data for display is provided in a format that does not require conversion from raw sensor data to the clinical information typically presented by the monitor. Further, the systems may be distributed to end users for training purposes without concern for inappropriate use of or modification of the data processing algorithms.

The clinical acceptance tools provided herein may display medical monitoring information based on collected data from one or more sensors. This data may be stored with or accessed by the clinical acceptance tool in a format that is ready for display with minimal additional processing. Further, the data may be associated with a particular window of time. In certain embodiments, an experimental algorithm or monitoring feature may be provided as part of the displayed data on the clinical acceptance tool. Such experimental features may also be displayed with a benchmark parameter or data set that a clinician may be more familiar with to demonstrate how the new feature may be used. In such embodiments, the experimental data and the benchmark data are representative of a single patient over a particular period of time. Accordingly, when the experimental data is displayed with the benchmark data by the clinical acceptance tool, the end user may directly compare the experiment feature with its clinical benchmark. In other embodiments, the data accessed by the clinical acceptance tool may be empirical data or simulated data. In particular, simulated data may be used to create training scenarios for the benefit of the end user.

As noted, caregivers or other end users may use the clinical acceptance tool to become more familiar with a new indicator or parameter. In addition, the clinical acceptance tool may be used in lieu of or in conjunction with passive instruction techniques, such video demonstrations, textual based instruction, and demonstrations. Further, the clinical acceptance tool may be used to gather feedback on particular features of the monitoring data and/or its associated graphical user interface. Accordingly, in particular embodiments, the clinical acceptance tool may be used during an experimental phase for a new parameter. Rather than developing more complex training materials that may become outdated as the product changes, the clinical training tool may be a relatively rapid and low-cost solution for introducing new features in development.

With the foregoing in mind, FIG. 1 is an illustration of an end user interface for the clinical acceptance system 10, which may be implemented via a general purpose computer 12. The clinical acceptance system 10 is capable of generating an output that represents an output of a patient monitor. However, this output may be isolated from the monitor itself and displayed on a general purpose computer. In this mariner, the system 10 provides a user-friendly monitor display that may be used for training or collecting user feedback. Such embodiments may be particularly advantageous for the display of clinical monitoring data associated with new or upgraded monitoring features. Rather than training materials that incorporate a static screenshot or dummy training mode, the clinical acceptance system 10 provides a more realistic context for the displayed data. Accordingly, the clinical acceptance system 10 includes a display 14 and user inputs 16, which may include a mouse, track pad, keyboard, touch screen, etc. The clinical acceptance system 10 may provide a simulator user, such as a caregiver, student, doctor, nurse, or medical technician, with graphical outputs 20. As will be discussed in more detail below, the graphical outputs 20 may include various graphical user interfaces representative of the medical device that is being simulated. In addition, the acceptance system 10 may be used with any suitable computer capable of displaying monitoring data. Such computers may include personal computers, off-the-shelf computers, multipurpose computers, laptops, desktop computers, notebooks, handheld device, mobile communication devices, or any suitable computing device. In other embodiments, the system 10 may be part of a modified medical device, such as a pulse oximetry monitor. In such embodiments, the system 10 may be accessible via an experimental or demo setting of medical device and may provide information related to proposed monitoring upgrades, e.g., new parameters.

Figure 2:
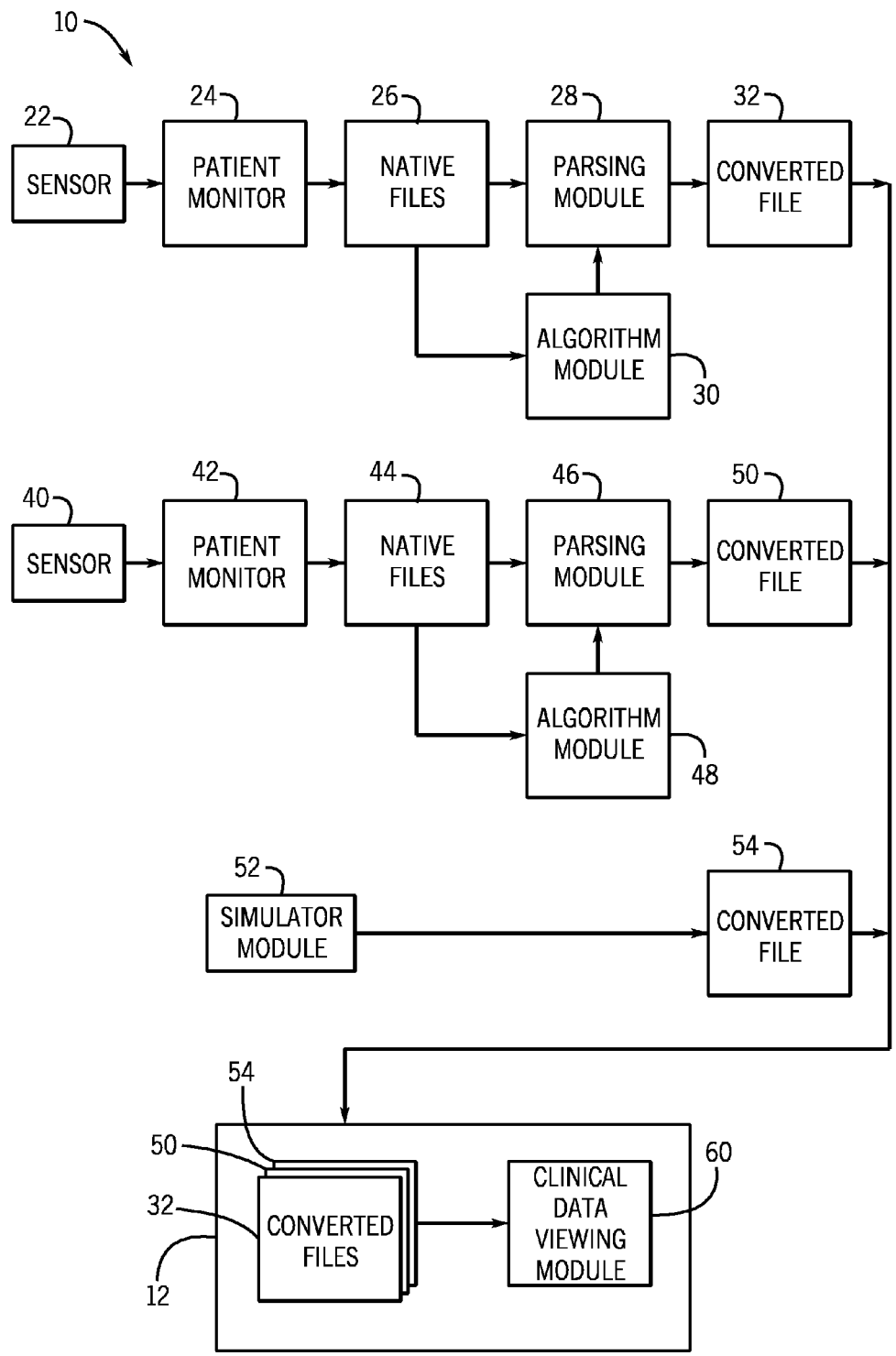
FIG. 2 is a block diagram of a clinical acceptance system in accordance with embodiments.

FIG. 2 is a block diagram of an example of a clinical acceptance system 10. It should be understood that, in certain embodiments, the system 10 may include all or some of the depicted components in any suitable arrangement. To generate an output that may be viewed and interpreted by the user, the system 10 may incorporate data collected from a medical sensor, e.g., sensor 22. For example, the sensor 22 is applied to a patient for monitoring and provides an output to a patient monitor 24, which is stored on the monitor in a native file format 26, which may be accessed and provided to the system 10 for further processing. In other embodiments, the sensor data may be provided to the system 10 in real time. The native file 26 from the patient monitor 24 includes raw data, e.g., absorption data, that is associated with a particular patient for a particular time frame. In certain embodiments, the time information is embedded in the native file 26 itself. In other embodiments, time information may be provided from a separate input, e.g., a clock associated with the monitor 24 or a user input. Further, the native file 26 may be raw data or preprocessed data.

The native file 26 is accessed by a parsing module 28, which is capable of reading the file format provided by the monitor and applying additional information, such as time information, and an algorithm module 30. The algorithm module is capable of processing the native file 26 to generate an output that is representative of an output that may be displayed on the monitor 24. For example, in a particular embodiment, the native file 26 may include absorption information. The absorption information is processed and correlated to a physiological parameter such as oxygen saturation. In particular embodiments, the physiological parameter may be a numerical output, e.g., a saturation index, or may be a graph or plot of numerical outputs over a period of time, e.g., a trend. The output of the algorithm module 30 is passed to the parsing module 28 to generate a converted file 32 that is capable of being displayed by the user interface computer 12. The converted file 32 may be accessed or stored by the computer 12 in isolation from its algorithm logic. In embodiments in which the output of the algorithm module 30 is a new or experimental monitoring feature, the computer 12 or software including the converted file 32 and a viewing tool may be distributed to the end user without the end user having access to any experimental algorithms. In particular, such an arrangement allows the end user to become familiar with a new user interface, e.g., a new parameter, while the algorithm itself is being tested and developed. In this manner, clinical acceptance for a new feature may progress more rapidly because the end user may be generally familiar with the displayed output even before the algorithm is finalized.

For embodiments in which a new monitoring feature replaces the functionality of a clinically familiar parameter or augments the information provided by such a parameter, it may be advantageous to include the familiar parameter in the displayed output of the clinical acceptance system 10. For example, the clinically familiar parameter may serve as a benchmark to facilitate understanding of how information from the experimental parameter may be applied. In certain embodiments, the system 10 may be capable of accessing data from additional sensors, e.g., sensor 40, that provide information related to the clinically familiar parameter. These sensors are operatively connected to either the monitor 24 or other dedicated monitors, e.g., patient monitor 42. A native file 44 representative of the sensor 40 may be parsed via parsing module 46 and processed by algorithm module 48 to provide a converted file 50 output for display. As noted, the sensor 22 may have different functionality than the sensor 40. Accordingly, it is contemplated that the algorithm module 48 may have different processing steps than the algorithm module 30. For example, the sensor 22 may be a photoplethysmography sensor and the sensor 40 may be a carbon dioxide sensor capable of determining an end tidal carbon dioxide during a ventilation cycle.

To provide meaningful feedback to the end user, the sensor 40 may be applied to the same patient and the same time as the sensor 22. In this manner, the outputs of these sensors may be directly compared. Accordingly, native file 44 may be from the same patient over an overlapping time frame as the native file 26. Where multiple native files from multiple patients are converted by the system 10, native files that are associated with one another (e.g., same patient) may be marked as such or otherwise bundled together in a single file. Further, because the sensors 22 and 40 may be of different types, these native files may be in entirely different formats, with different sampling rates and time windows. In such embodiments, one or both of the native files 26 and 44 may be resampled at the same rate by the parsing modules 28 and 46 prior to processing. The rate of resampling may be dictated by the lowest sampling rate between the native files 26 and 44. However, in certain embodiments, when the sampling rates are divergent, a lower sampling rate may be artificially increased by extrapolating sampling points. In addition, one or both of the native files 26 and 44 may be cropped to approximately the same time window. This may be accomplished using time information from the monitors 24 and 42.

As an alternative to accessing native files, the data may include simulated data. The system 10 may include a simulator module 52 that may allow a user to experience clinical conditions that may be relatively exaggerated for training purposes. For example, a simulated data set may include respiration rate values that may be physiologically unlikely for an actual patient but that may be useful for showing the difference between an, experimental parameter and a benchmark parameter. In one embodiment, the experimental parameter and the benchmark parameter may have high correlation across many patient types. In other embodiments, the experimental parameter may be more appropriate for certain types of patients or may be less prone to artifacts in conditions in which a benchmark parameter is less robust. The output of the simulator module 52 may be a converted file 54 that is in a format that is easily displayed. Alternatively, the simulator module 52 may generate data that is similar in format to a native file 26 or 50. In such embodiments, the system 10 may pass the output of the simulator module 52 to appropriate parsing and algorithm modules for further processing.

The system 10 includes an end user interface 12 on which the converted files may be displayed. Depending on the file format of these files, the computer 12 also includes a compatible clinical data viewing module 60. As depicted in FIG. 2, in addition to the end user interface, e.g., computer 12, the clinical acceptance system 10 may also include, among other things, the display 14, user inputs 16, one or more processors, a memory, non-volatile storage, and stored input files. While the computer 12 may be a separable component of the system 10, the depicted components and modules may be arranged in any suitable configuration. The various functional blocks shown in FIG. 2 may include hardware elements (including circuitry), software elements (including computer code stored on a computer-readable medium) or a combination of both hardware and software elements. Further, FIG. 2 is only one example of a particular implementation and is merely intended to illustrate the types of components that may be present in the system. In one implementation, the system 10 may be developed and implemented using open source tools. Such a system may be developed as a web-based application, allowing distributed access or use of the application. For example, such an implementation may be developed using one or more of Java, Java server pages (JSP), structured query language (SQL), extensible markup language (XML), XML user interface language (XUL) and/or scalable vector graphics (SVG) technologies. In an alternate implementation, the system 10 may include instructions that may be executed by an associated processor, and stored on a non-volatile storage media, such as a CD-ROM or hard drive.

The converted files (e.g., files 32, 50, or 54) may comprise various forms including: a text file, a binary file, an ASCII file, a formatted text file, an image file, a MATLAB file, or any suitable form for display. The converted files may be stored on a non-volatile storage media associated with the computer 12, or may be downloaded from an outside source through a network connection. In some embodiments, the system 10 may intake the converted files through an import screen. In alternative embodiments, the system 10 may select a file from a plurality of stored files based upon a user selection of physiological conditions, e.g. conditions listed in the import screen of the system 10. For example, the user may desire to view monitoring data associated with the conditions of severe sleep apnea. The user may select "sleep apnea" from the list of physiological conditions, and the system 10 will import either a simulated or patient data file corresponding to that condition.

Figure 3:
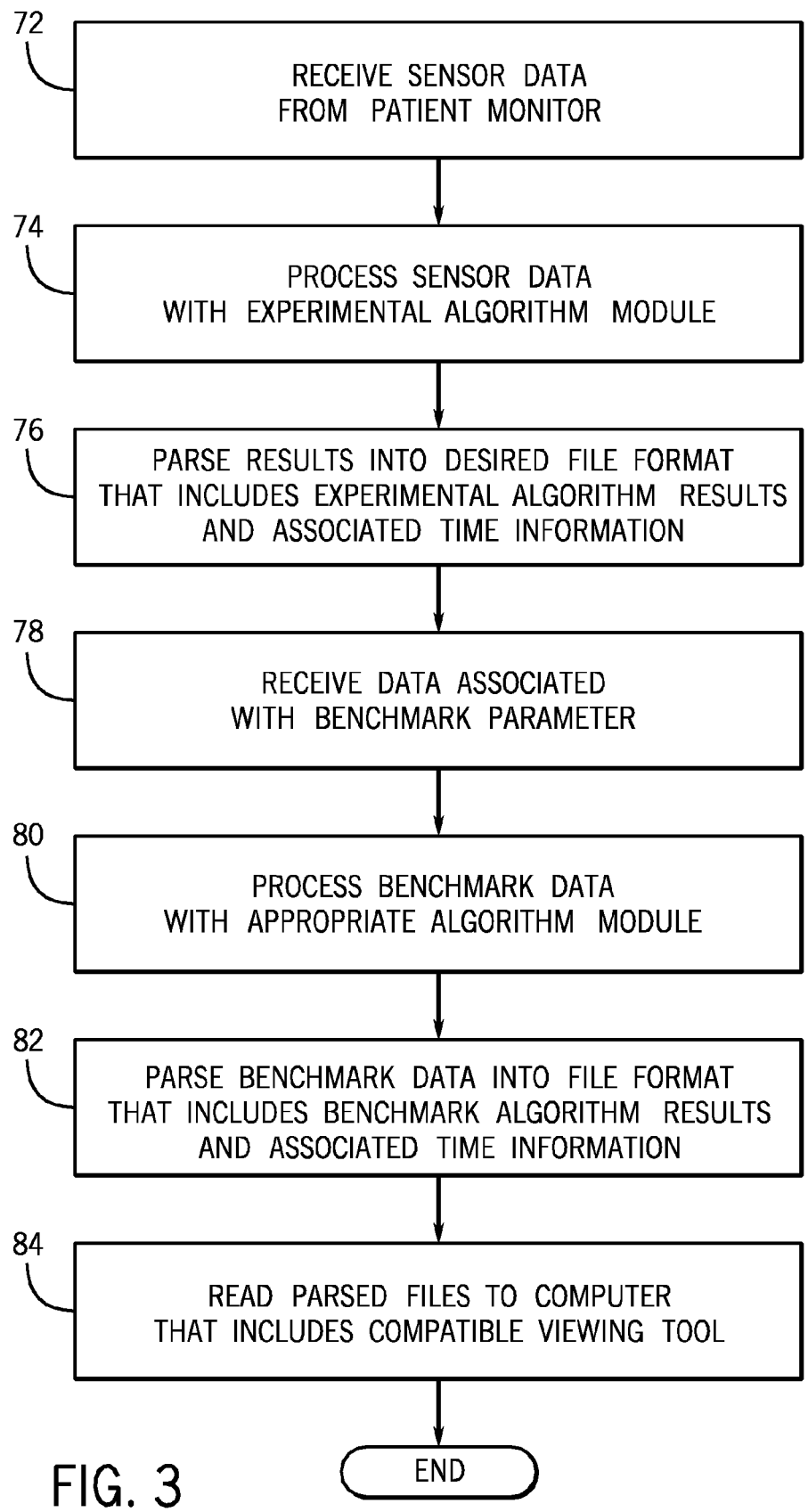
FIG. 3 is a flowchart depicting a method of converting monitor data in accordance with embodiments.

An example of a simulation method 70 is illustrated in the flowchart depicted in FIG. 3. The method 70 may be performed as an automated procedure by a system, such as a system 10. In addition, certain steps of the method may be performed by a processor, or a processor-based device that may be part of the system 10 and that includes instructions for implementing certain steps of the method 70. The simulation method 70 begins at block 72 when the system 10 receives input related from a medical monitor, e.g., monitor 24, in the form of a raw sensor data. In alternative embodiments, the data provided by the medical monitor may be in the form of preprocessed or simulated data.

At block 74, the system 10 applies appropriate processing instructions to the data to generate an output that is representative of the output of the monitor. These algorithms may be identical to the algorithms typically used by the monitor itself or may be modified or altered in some way. Based at least in part upon the native files (e.g., the sensor data), the algorithm module may calculate the parameter of interest using various algorithms. In one embodiment, the algorithms may incorporate instructions such as those employed by the Nellcor™ N-600x™ pulse oximetry monitor. These algorithms may also employ certain coefficients, which may be stored in a memory or other suitable computer-readable storage medium and accessed and operated according to processor instructions. In one embodiment, the algorithm module includes an experimental algorithm. Experimental algorithms may include algorithms that have not been approved by a regulatory agency, algorithms that are in a beta testing mode, algorithms for new or modified parameters, or next generation algorithms.

At block 76 the system parses the output of the experimental algorithm module into a desired file format that includes time information. In addition, in block 78, the system receives benchmark data. Benchmark data may refer to data from a sensor and monitor that correlates to a clinically familiar physiological parameter. For example, a benchmark parameter may be a standard of care, part of an approved medical monitoring system, or a parameter for comparison. In certain embodiments, the benchmark parameter may be a current generation parameter while the experimental parameter is a next generation parameter. The benchmark sensor data may be collected from or representative of the same patient during an overlapping time window. The benchmark data may be processed according to an appropriate algorithm module at block 80 and parsed into a converted file format with associated time data at block 82. These converted files may be read to an appropriate computer, e.g., computer 12, or other device for eventual viewing by an end user at step 84.

Figure 4:
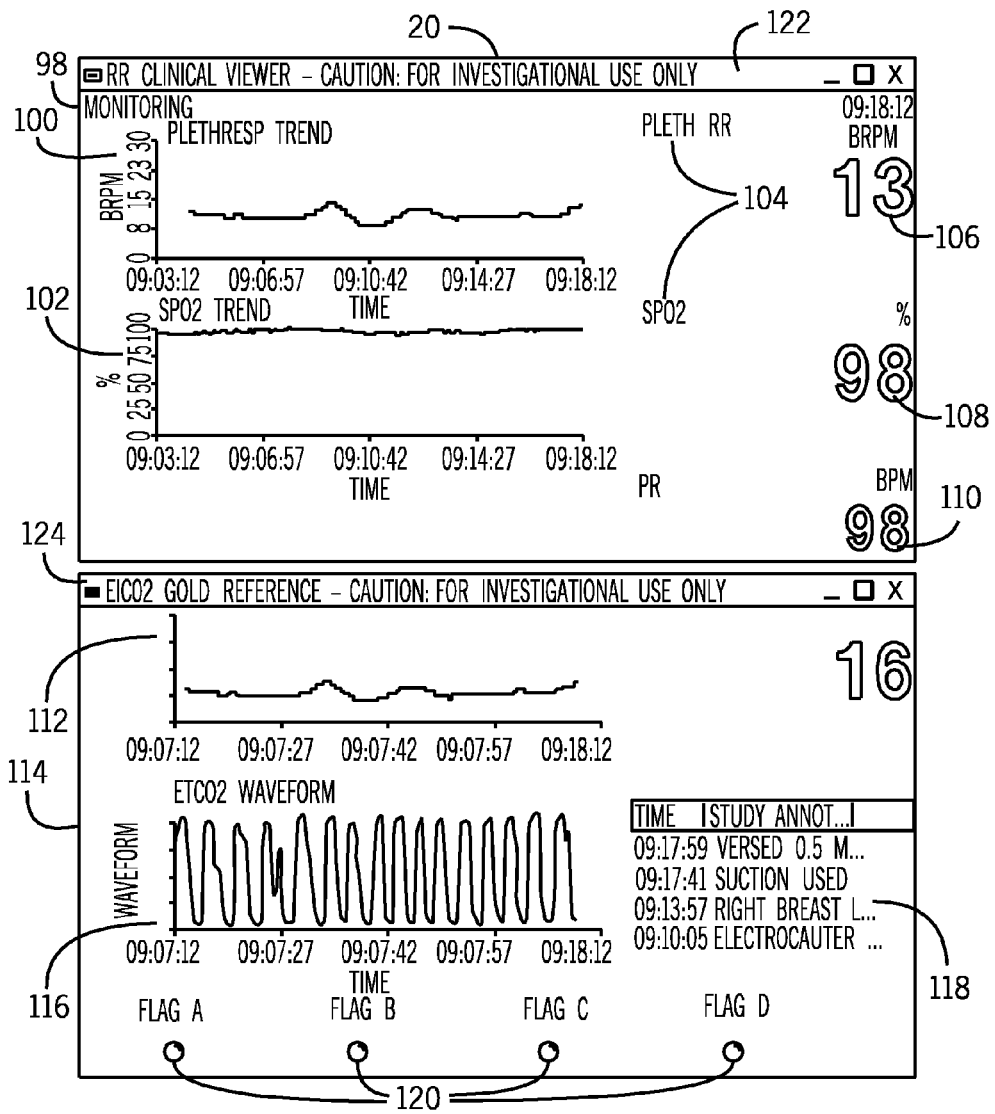
FIG. 4 depicts an example of clinical acceptance display featuring an experimental parameter output and a benchmark parameter output.
Figure 5:
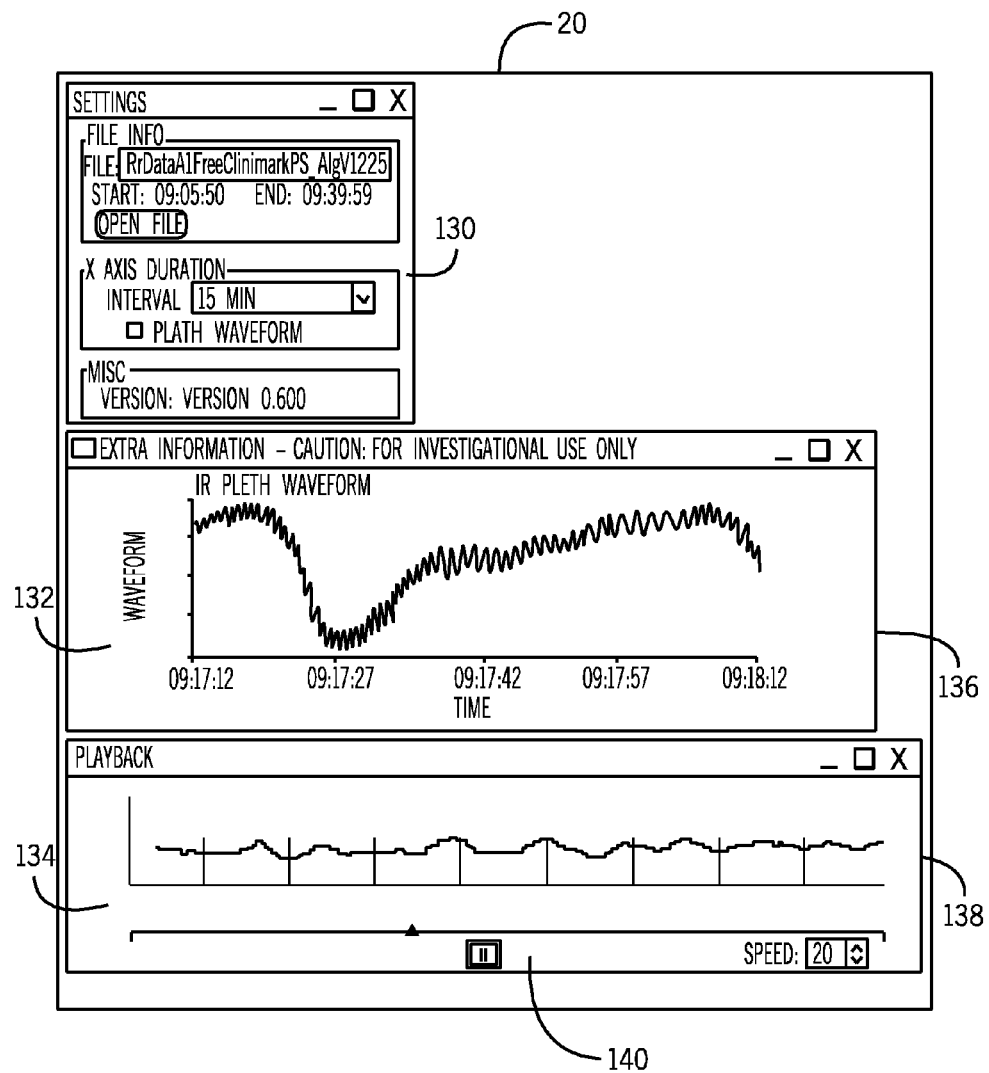
FIG. 5 depicts an example of a clinical acceptance system display including additional review features.

In particular, the system 10 may facilitate understanding and clinical acceptance of a new clinical monitoring parameter. To that end, the system 10 may provide one or more display screens 20 that are representative of the data that will be displayed on a patient monitor. In addition, this data may be displayed along with training or supplemental data. FIGS. 4-5 illustrate different types of displays that may be used with the system 10. While the illustrated embodiments relate to respiration rate, it should be understood that the present techniques may be used in conjunction with other parameters. For example, the medical parameters of interest may include oxygen saturation, blood or tissue constituent concentration, hemodynamic parameters, cardiac parameters, or respiratory parameters. Depicted is a dual window view that includes an upper window 98. In the depicted embodiment, the parameter of interest, a respiration trend calculated based on a plethysmographic waveform signal, is displayed in trend view in plot 100. The plot 100 includes an indication of breaths per minute (BrPM) on the Y-axis over time on the x-axis. Also displayed is a plot 102 of an oxygen saturation trend over the same time window as the respiration rate trend. The plots may be labeled as appropriate, e.g., with text 104. Numeric indicators 106, 108, and 110 for respiration rate, oxygen saturation, and pulse rate are also provided. In the depicted embodiment, the oxygen saturation plot 102 and the oxygen saturation indicator 108 and pulse rate indicator 110 are generally familiar to an experienced caregiver while the respiration rate plot 100 and the respiration rate indicator 106 are new features. Accordingly, the display 98 may be used to familiarize an end user with the relative positioning of the new parameter, respiration rate, and the types of data provided to convey information about the parameter (e.g., a trend plot and a numeric indicator). Such training is beneficial because clinicians tend to rely on quick glances at display screens and are accustomed to finding certain parameters in certain locations.

While the respiration rate plot 100 is displayed concurrently with an oxygen saturation plot 102, oxygen saturation is not typically regarded as a benchmark parameter for respiration rate. That is, as shown, the oxygen saturation trend remains relatively stable while the respiration rate varies. While these parameters are related (e.g., decreased respiration rate may be correlated to lower oxygen saturation), they do not exhibit close correlation. One method of determining respiration rate is evaluating a patient's end tidal carbon dioxide concentration via capnography. In capnography, a carbon dioxide sensor monitors the partial pressure of carbon dioxide in the respiratory gases. By monitoring the carbon dioxide changes during the breath cycle, the number of breaths per minute may be determined. An end-tidal carbon dioxide plot 112 is shown in lower window 114. The end-tidal carbon dioxide plot 112 may serve as a benchmark for the respiration rate as calculated via the pleth waveform. Accordingly, a clinician may note that the end-tidal carbon dioxide plot 112 correlates closely to the respiration rate plot 100 above for the same patient over the same time frame. In certain embodiments, the system 10 may display a correlation metric or indicator for the experimental parameter and the benchmark parameter. Also shown, for reference, is the waveform signal 116 for the end-tidal carbon dioxide plot. Additional information may be displayed in sidebar 118 and may include time-stamped events, including patient movement or drug administration, events that may introduce noise, such as suctioning of a tracheal tube 112, and any alarms or specific conditions (e.g., clinical conditions or patient conditions) designated by the monitor, which may be shown as flags 120. The windows 98 and 114 may be labeled, e.g., labels 122 and 124) to indicate which window includes the experimental parameter of interest versus the benchmark parameter. In certain embodiments, the lower window 114 may be closed and removed from view if the clinician has reviewed its contents.

FIG. 5 illustrates an additional display output 20 that provides additional graphical windows that may supplement the experimental parameter information. Such displays may include a file information window 130, a waveform window 132 that includes the pleth signal 136 from which the respiration rate was calculated, a playback window 134 that includes a respiration rate plot 138 with playback controls 140. In the depicted embodiment, the healthcare professional may alter the playback rate of the simulation. For example, the user may pause the simulation or replay a portion of the simulation with either the same or different alarm configuration settings. Further, the file information window 130 may allow the user to select a different file from a different patient or simulated data set.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims.

What is claimed is:

1. A system, comprising:
a processor configured to execute instructions for:
receiving a first data set from a medical monitor, wherein the first data set comprises data representing a physiological parameter from a patient over a predetermined time period at a first sampling rate;
receiving a second data set from a second monitor, wherein the second data set comprises data representing the physiological parameter from the patient over the predetermined time period at a second sampling rate, wherein the second sampling rate is different from the first sampling rate;
resampling the first data set at the second sampling rate to generate a first resampled data set;
determining a first trend of the value of the physiological parameter over the predetermined time period based on the first resampled data set using a first algorithm;
determining a second trend of the value of the physiological parameter over the predetermined time period based on the second data set using a second algorithm; and
generating a first output comprising the first trend of the physiological parameter determined based on the first resampled data set and a second output comprising the second trend of the physiological parameter determined based on the second data set.

2. The system of claim 1, wherein the physiological parameter comprises respiration rate.

3. The system of claim 1, wherein the physiological parameter comprises a respiratory rate trend.

4. The system of claim 1, wherein the first data set comprises data collected by a photoplethysmography sensor.

5. The system of claim 4, wherein the photoplethysmography sensor comprises a pulse oximetry sensor.

6. The system of claim 1, wherein the second data set comprises data collected by a carbon dioxide sensor.

7. The system of claim 1, wherein the second algorithm determines the physiological parameter based on an end-tidal carbon dioxide concentration.

8. The system of claim 1, wherein the first sampling rate is lower than the second sampling rate.

9. The system of claim 1, comprising providing the first output and the second output to a computer capable of displaying the first output and the second output.

10. The system of claim 9, wherein the computer does not include instructions for executing the first algorithm or the second algorithm.

11. The system of claim 1, wherein the first algorithm or the second algorithm comprises an experimental algorithm.

12. The system of claim 11, wherein the first algorithm comprises the experimental algorithm and the second algorithm comprises a benchmark algorithm.

13. The system of claim 1, wherein one or both of the first data set and the second data set comprise a simulated data set.

14. The system of claim 1, wherein the first data set comprises data collected by a first type of medical sensor and wherein the second data set comprises data collected by a second type of medical sensor, wherein the first type of medical sensor is different than the second type of medical sensor.

15. A system, comprising:
 a processor configured to execute instructions for:
  receiving a first data set from a medical monitor, wherein the first data set comprises data representing a physiological parameter from a patient over a predetermined time period at a first sampling rate;
  receiving a second data set from a second monitor, wherein the second data set comprises data representing the physiological parameter from the patient over the predetermined time period at a second sampling rate, wherein the second sampling rate is different from the first sampling rate;
  resampling the first data set and the second data set at a third sampling rate different from the first sampling rate and the second sampling rate to generate a first resampled data set and a second resampled data set;
  determining a first trend of the value of the physiological parameter over the predetermined time period based on the first resampled data set using a first algorithm;
  determining a second trend of the value of the physiological parameter over the predetermined time period based on the second resampled data set using a second algorithm; and
  generating a first output comprising the first trend of the physiological parameter determined based on the first resampled data set and a second output comprising the second trend of the physiological parameter determined based on the second resampled data set.

16. The system of claim 15, wherein the first sampling rate is lower than the second sampling rate.

17. The system of claim 15, wherein the first sampling rate and the second sampling rate are higher than the third sampling rate.

18. The system of claim 15, comprising providing the first output and the second output to a computer capable of displaying the first output and the second output.

19. The system of claim 15, wherein the first algorithm or the second algorithm comprises an experimental algorithm.

20. The system of claim 15, wherein the first algorithm or the second algorithm comprises a benchmark algorithm.

21. The system of claim 15, wherein one or both of the first data set and the second data set comprise a simulated data set.

* * * * *